US 7,060,992 B1
United States Patent
Barney

(10) Patent No.: US 7,060,992 B1
(45) Date of Patent: Jun. 13, 2006

(54) SYSTEM AND METHOD FOR BIOAEROSOL DISCRIMINATION BY TIME-RESOLVED FLUORESCENCE

(75) Inventor: William S. Barney, Bedford, MA (US)

(73) Assignee: Tiax LLC, Cambridge, MA (US)

( * ) Notice: Subject to any disclaimer, the term of this patent is extended or adjusted under 35 U.S.C. 154(b) by 274 days.

(21) Appl. No.: 10/797,716

(22) Filed: Mar. 10, 2004

Related U.S. Application Data

(60) Provisional application No. 60/453,325, filed on Mar. 10, 2003.

(51) Int. Cl.
*G01N 21/64* (2006.01)

(52) U.S. Cl. .............................. 250/458.1; 250/459.1; 250/461.1; 250/461.2

(58) Field of Classification Search ............. 250/459.1, 250/458.1, 461.1, 462.1, 461.2
See application file for complete search history.

(56) References Cited

U.S. PATENT DOCUMENTS

| | | |
|---|---|---|
| 3,566,114 A | 2/1971 | Brewer |
| 3,716,426 A | 2/1973 | Becker |
| 3,717,097 A | 2/1973 | Wronka et al. |
| 3,750,585 A | 8/1973 | Feldman |
| 3,756,720 A | 9/1973 | Skala |
| 3,760,735 A | 9/1973 | Schmitt |
| 3,768,908 A | 10/1973 | Zaromb |
| 3,772,200 A | 11/1973 | Livesay |
| 3,897,284 A | 7/1975 | Livesay |
| 3,961,106 A | 6/1976 | Heytmeijer et al. |
| 3,962,412 A | 6/1976 | Wolfangel |
| 3,967,990 A | 7/1976 | Ryan et al. |
| 3,991,626 A | 11/1976 | Shair |
| 3,993,838 A | 11/1976 | Heytmeijer et al. |
| 4,010,250 A | 3/1977 | Parikh et al. |
| 4,013,490 A | 3/1977 | Ryan et al. |
| 4,013,888 A | 3/1977 | Macias et al. |
| 4,018,635 A | 4/1977 | Ryan et al. |
| 4,019,053 A | 4/1977 | Levine |
| RE29,334 E | 8/1977 | Ryan et al. |
| 4,053,433 A | 10/1977 | Lee |
| 4,057,616 A | 11/1977 | Wolfangel |
| 4,058,732 A | 11/1977 | Wieder |
| 4,063,510 A | 12/1977 | Ishii et al. |
| 4,131,064 A | 12/1978 | Ryan et al. |
| 4,197,104 A | 4/1980 | Krystyniak et al. |

(Continued)

FOREIGN PATENT DOCUMENTS

DE 19949658 5/2001

(Continued)

OTHER PUBLICATIONS

S.W. Allison et al., "Phosphor Thermometry Techniques for the Realization of Thermal Standards," http://www.isa.org/journals/intech/ISA-02-P218.pdf; publication date unknown.

(Continued)

*Primary Examiner*—David Porta
*Assistant Examiner*—Christopher Webb
(74) *Attorney, Agent, or Firm*—Lowrie, Lando & Anastasi, LLP

(57) ABSTRACT

The systems and methods of the invention utilize time-resolved techniques to deconvolve a measured response to characterize the nature of particles. The measured response is deconvolved into a scatter component and a fluorescence component. The fluorescence component is further characterized into biological and non-biological components. A discriminant vector is mapped to characterize the nature of the particle.

26 Claims, 9 Drawing Sheets

U.S. PATENT DOCUMENTS

| | | | |
|---|---|---|---|
| 4,198,307 A | 4/1980 | Berkowitz et al. |
| 4,251,726 A | 2/1981 | Alvarez |
| 4,256,038 A | 3/1981 | Dietz et al. |
| 4,329,393 A | 5/1982 | LaPerre et al. |
| 4,359,399 A | 11/1982 | Boyars |
| 4,363,678 A | 12/1982 | Nishimura et al. |
| 4,363,965 A | 12/1982 | Soberman et al. |
| 4,390,452 A | 6/1983 | Stevens |
| 4,399,226 A | 8/1983 | Danielson et al. |
| 4,423,152 A | 12/1983 | Lewis et al. |
| 4,441,943 A | 4/1984 | Kydd |
| 4,455,179 A | 6/1984 | Yamaguchi et al. |
| 4,510,929 A | 4/1985 | Bordoni et al. |
| 4,537,645 A | 8/1985 | Yamaguchi et al. |
| 4,598,704 A | 7/1986 | Bordoni et al. |
| 4,603,575 A | 8/1986 | Rahn et al. |
| 4,640,035 A | 2/1987 | Kind et al. |
| 4,651,010 A | 3/1987 | Javan |
| 4,652,395 A | 3/1987 | Marcina et al. |
| 4,654,165 A | 3/1987 | Eisenberg |
| 4,676,642 A | 6/1987 | French |
| 4,703,753 A | 11/1987 | Bordoni et al. |
| 4,741,331 A | 5/1988 | Wunderlich |
| 4,744,919 A | 5/1988 | O'Holleran |
| 4,750,837 A | 6/1988 | Gifford et al. |
| 4,939,372 A | 7/1990 | Schvoerer et al. |
| 5,024,753 A | 6/1991 | Chriswell et al. |
| 5,110,204 A | 5/1992 | Miles et al. |
| 5,148,173 A | 9/1992 | Rouse et al. |
| 5,158,889 A | 10/1992 | Hirako et al. |
| 5,168,212 A | 12/1992 | Byerley, III et al. |
| 5,216,086 A | 6/1993 | Fong et al. |
| 5,221,927 A | 6/1993 | Palmer |
| 5,245,038 A | 9/1993 | Hale et al. |
| 5,252,740 A | 10/1993 | Hale et al. |
| 5,294,796 A | 3/1994 | Fee |
| 5,298,751 A | 3/1994 | Fee et al. |
| 5,397,819 A | 3/1995 | Krutak et al. |
| 5,409,839 A | 4/1995 | Balestrieri et al. |
| 5,418,855 A | 5/1995 | Liang et al. |
| 5,461,136 A | 10/1995 | Krutak et al. |
| 5,525,377 A | 6/1996 | Gallagher et al. |
| 5,526,676 A | 6/1996 | Solheim et al. |
| 5,532,598 A | 7/1996 | Clark, Jr. et al. |
| 5,639,984 A | 6/1997 | Nielson |
| 5,648,914 A | 7/1997 | Bauer et al. |
| 5,659,147 A | 8/1997 | Rouse et al. |
| 5,677,187 A | 10/1997 | Anderson, II et al. |
| 5,682,038 A | 10/1997 | Hoffman |
| 5,701,012 A | 12/1997 | Ho |
| 5,703,229 A | 12/1997 | Krutak et al. |
| 5,714,387 A | 2/1998 | Fowee et al. |
| 5,760,394 A | 6/1998 | Welle |
| 5,767,519 A | 6/1998 | Gelbwachs |
| 5,786,219 A | 7/1998 | Zhang et al. |
| 5,828,452 A | 10/1998 | Gillispie et al. |
| 5,849,590 A | 12/1998 | Anderson, II et al. |
| 5,895,922 A | 4/1999 | Ho |
| 5,909,278 A | 6/1999 | Deka et al. |
| 5,955,737 A * | 9/1999 | Hallidy et al. ........... 250/458.1 |
| 5,999,652 A | 12/1999 | Bushman |
| 6,007,744 A | 12/1999 | Nacker |
| 6,025,200 A | 2/2000 | Kaish et al. |
| 6,098,018 A | 8/2000 | Welsh et al. |
| 6,137,584 A | 10/2000 | Brand et al. |
| 6,142,025 A | 11/2000 | Zborowski et al. |
| 6,165,740 A | 12/2000 | Fukuda et al. |
| 6,194,731 B1 | 2/2001 | Jeys et al. |
| 6,200,628 B1 | 3/2001 | Rozumek et al. |
| 6,266,428 B1 | 7/2001 | Flanigan |
| 6,380,547 B1 | 4/2002 | Gonzalez et al. |
| 6,399,390 B1 | 6/2002 | Kantzas et al. |
| 6,432,715 B1 | 8/2002 | Nelson et al. |
| 6,455,851 B1 | 9/2002 | Lord et al. |
| 6,490,530 B1 | 12/2002 | Wyatt |
| 6,514,617 B1 | 2/2003 | Hubbard et al. |
| 6,528,318 B1 | 3/2003 | Miragliotta et al. |
| 6,603,549 B1 | 8/2003 | Haas et al. |
| 6,608,677 B1 | 8/2003 | Ray et al. |
| 6,610,351 B1 | 8/2003 | Shchegolikhin et al. |
| 6,617,591 B1 | 9/2003 | Simonson et al. |
| 6,627,113 B1 | 9/2003 | Kijima et al. |
| 6,630,299 B1 | 10/2003 | Carrión et al. |
| 6,647,649 B1 | 11/2003 | Hunt et al. |
| 6,680,778 B1 | 1/2004 | Hinnrichs et al. |
| 6,692,031 B1 | 2/2004 | McGrew |
| 6,710,871 B1 | 3/2004 | Goix |
| 2002/0021003 A1 | 2/2002 | McGrew |
| 2002/0025490 A1 | 2/2002 | Shchegolikhin et al. |
| 2002/0028434 A1 | 3/2002 | Goix et al. |
| 2002/0063863 A1 | 5/2002 | Kask |
| 2002/0129523 A1 | 9/2002 | Hunt |
| 2002/0158211 A1 | 10/2002 | Gillispie |
| 2002/0174794 A1 | 11/2002 | Lowden et al. |
| 2003/0021998 A1 | 1/2003 | Hubbard et al. |
| 2003/0036201 A1 | 2/2003 | Nelson et al. |
| 2003/0109049 A1 | 6/2003 | Miragliotta et al. |
| 2003/0177842 A1 | 9/2003 | Swartzel et al. |
| 2003/0193338 A1 | 10/2003 | Krasnobaev et al. |
| 2004/0005635 A1 | 1/2004 | Goix et al. |
| 2004/0007675 A1 | 1/2004 | Gillespie et al. |
| 2004/0026684 A1 | 2/2004 | Empedocles |
| 2004/0058058 A1 | 3/2004 | Shchegolikhin et al. |
| 2004/0067360 A1 | 4/2004 | Steenblik et al. |
| 2004/0098891 A1 | 5/2004 | Hunt et al. |
| 2004/0155191 A1 | 8/2004 | Stedman et al. |
| 2005/0243307 A1 * | 11/2005 | Silcott et al. .................. 356/73 |

FOREIGN PATENT DOCUMENTS

| | | |
|---|---|---|
| EP | 0 085 414 A1 | 1/1983 |
| EP | 0 118 667 A1 | 1/1984 |
| EP | 0 474 264 A | 3/1992 |
| EP | 0 927 750 B1 | 4/2004 |
| WO | WO 99/34315 A2 | 7/1999 |
| WO | WO 00/71966 A2 | 11/2000 |
| WO | WO 00/75895 A1 | 12/2000 |
| WO | WO 01/37207 A1 | 5/2001 |

OTHER PUBLICATIONS

R.A. Keller et al., "Single-Molecule Fluorescence Analysis in Solution," *Applied Spectroscopy, The Society for Applied Spectroscopy*, Jul. 1, 1996, pp. 12A-32A, vol. 50, No. 7, Baltimore, US.

M. Musolino et al., "An integrated Instrumentation for Light-Scattering and Time-Resolved Fluorescence Measurements," *Review of Scientific Instruments, American Institute of Physics*, Mar. 1, 1995, pp. 2405-2410, vol. 66, No. 3, New York, US.

S.W. Allison et al., "A Wide-Range Phosphor Thermometry Technique," prepared by the Oak Ridge National Laboratory, Oak Ridge, TN, managed by Lockheed Martin Energy Research Corp. for the U.S. Dept. of Energy under contract DE-AC05-96OR22464, Mar. 1998.

W. Allison, "Phosphor thermometry - The essential features are in place for realizing a temperature scale in terms of atomic quantities," published at http://www.isa.org/INTECHTemplate.cfm?Section=Article Index &template=/ContentManagement/ContentDisplay.cfm&ContentID=25051, Apr. 1, 2003, pp. 1-5.

S.W. Allison et al., "Phospher Thermometry Techniques for the Realization of Thermal Standards," published at http://www.isa.org/journals/intech/ISA02-P218.pdf, publication date unknown.

M. Cates et al., "Phosphor Thermometry Tutorial", Oak Ridge National Laboratory, U.S. Dept. of Energy, UT-Battelle, (publication date unknown).

P. Decarlo et al., "Particle Morphology and Density Characterization by Combined Mobility and Aerodynamic Diameter Measurements Part 1: Theory", submitted to Aerosol Science & Technology on Jul. 2, 2004, pp. 1-75, (publication date unknown).

*Luminescent Materials*, Kirk-Othmer Concise Encyclopedia of Chemical Technology.-4$^{th}$ed. , p. 1219, 1999, John Wiley & Sons, Inc., Canada.

Pan, "Application of light-emitting diodes for aerosol fluorescence detection, " *OPTICS LETTERS*, Sep. 15, 2003, pp. 1707-1709, vol. 28, No. 18.

Wahl, "Laser-Based Diagnostics of Diamond Synthesis Reactors," High Temperature Gasdynamics Laboratory, Thermosciences Division, Dept. of Mechanical Engineering, Stanford University, U.S. Dept. of Energy, Report No. TSD-136 (2001).

US 6,780,301, 08/2004, Natan et al. (withdrawn)

* cited by examiner

SYSTEM AND METHOD FOR BIOAEROSOL DISCRIMINATION BY TIME-RESOLVED FLUORESCENCE

RELATED APPLICATION

This application claims priority under 35 U.S.C. § 119(e) to U.S. Provisional Application Ser. No. 60/453,325, entitled "Method for Bioaerosol Discrimination by Time-Resolved Laser Induced Fluorescence (TRILIF)," filed on Mar. 10, 2003, which is herein incorporated by reference in its entirety.

FEDERALLY SPONSORED RESEARCH

This invention was made with Government support under National Science Foundation SBIR Award #030211.

BACKGROUND OF INVENTION

1. Field of Invention

The present invention relates to classifying particles and, in particular, to utilizing time-based fluorescence techniques to characterize the biological nature of aerosol particles.

2. Discussion of Related Art

Detection of biological aerosol particles or bioaerosols can be important in many fields including, for example, agriculture, food processing, public health, worker safety, resident/patient safety, disease prevention and eradication, emergency response, homeland defense and counterterrorism, and military base and force protection because bioaerosols may be harmful to human or animal health. Intrinsic particle fluorescence is a method that be utilized to distinguish biological particles from non-biological background particles. However, atmospheric pollutants may also fluoresce and can cause fluorescence-based instruments to register false positive indications. Various systems and methods can be utilized to characterize the nature of aerosol particles. For example, common detectors, cue detectors or trigger detectors, are typically optical scattering particle counters equipped with laser-induced fluorescence detection devices. Typically in such a system, an ultraviolet laser beam excites a particle to be examined. The particle's resultant fluorescence can be dispersed into two detection channels, roughly divided between ultraviolet and visible wavelengths. The particle is thereafter classified as threatening or non-threatening according to its relative position on a three-dimensional graph of UV intensity, visible intensity, and scattering intensity. While progress has been made these detectors still suffer from potential interference due to background fluorescence.

For example, Brewer, in U.S. Pat. No. 3,566,114, discloses a method and means for detection of microorganisms in the atmosphere. Macias et al., in U.S. Pat. No. 4,013,888, disclose a monitor for atmospheric pollutants. Javan, in U.S. Pat. No. 4,561,010, discloses a method and apparatus for fluorescent sensing. Hirako et al., in U.S. Pat. No. 5,158,889, disclose a biological cell sorter. Ho, in U.S. Pat. Nos. 5,701,012 and 5,895,922, discloses fluorescent biological particle detection systems. Gillespie et al., in U.S. Pat. No. 5,828,452, disclose a spectroscopic system with a single converter and method for removing overlay in time of detected emissions. Zborowski et al., in U.S. Pat. No. 6,142,025, disclose a method for determining particle characteristics. Fukuda et al., in U.S. Pat. No. 6,165,740, disclose a method and device for flow-cytometric microorganism analysis. Jeys et al., in U.S. Pat. No. 6,194,731, disclose a bio-particle fluorescence detector. Ray et al., in U.S. Pat. No. 6,608,677, disclose a mini-LIDAR sensor for the remote stand-off sensing of chemical/biological substances and methods for sensing same. Simonson et al., in U.S. Pat. No. 6,617,591, disclose a method for remote detection of trace contaminants. Carrión et al., in U.S. Pat. No. 6,630,299, disclose fluorescence detection. Gillispie, in U.S. Patent Application Publication 2002/0158211, disclose a multi-dimensional fluorescence apparatus and method for rapid and highly sensitive quantitative analysis of mixtures.

SUMMARY OF INVENTION

In accordance with one or more embodiments, the present invention relates to a system for classifying aerosol particles. The system can comprise a detector capable of generating a signal corresponding to a composite emission decay profile of an emission from an aerosol particle and a means for deconvolving the signal into a discriminant vector that provides an indication of the nature of the aerosol particle.

In accordance with one or more embodiments, the present invention relates to a system for classifying aerosol particles. The system can comprise a detector capable of generating a signal corresponding to a composite emission decay profile of an emission from a sample of aerosol particles and a processor coupled to the detector to receive the signal. The processor can determine a scatter component and a fluorescence component of the composite emission decay profile.

In accordance with one or more embodiments, the present invention relates to a method of classifying an aerosol particle. The method can comprise measuring a composite emission decay profile of an emission from the aerosol particle, determining a biological fluorescence time constant of the composite emission decay profile, and determining a biological emission constant of the composite emission decay profile.

In accordance with one or more embodiments, the present invention relates to a method of classifying aerosol particles. The method can comprise stimulating the aerosol particles to promote radiation emission; measuring a composite emission decay profile of the radiation emission, the composite emission decay profile comprising a scatter component, a first fluorescence component, and a second fluorescence component; determining a scatter emission constant corresponding to the scatter component; determining a first fluorescence emission constant of the composite emission decay profile; and determining a second fluorescence emission constant of the composite emission decay profile.

In accordance with one or more embodiments, the present invention relates to a method of classifying an aerosol particle. The method can comprise measuring a composite emission from an aerosol particle, deconvolving the composite emission to determine a discriminant vector of the aerosol particle, and mapping the discriminant vector to provide an indication of the nature of the aerosol particle.

BRIEF DESCRIPTION OF DRAWINGS

The accompanying drawings, are not intended to be drawn to scale. In the drawings, each identical or nearly identical component that is illustrated in various figures is represented by a like numeral. For purposes of clarity, not every component may be labeled in every drawing. In the drawings:

DETAILED DESCRIPTION

Figure 1:
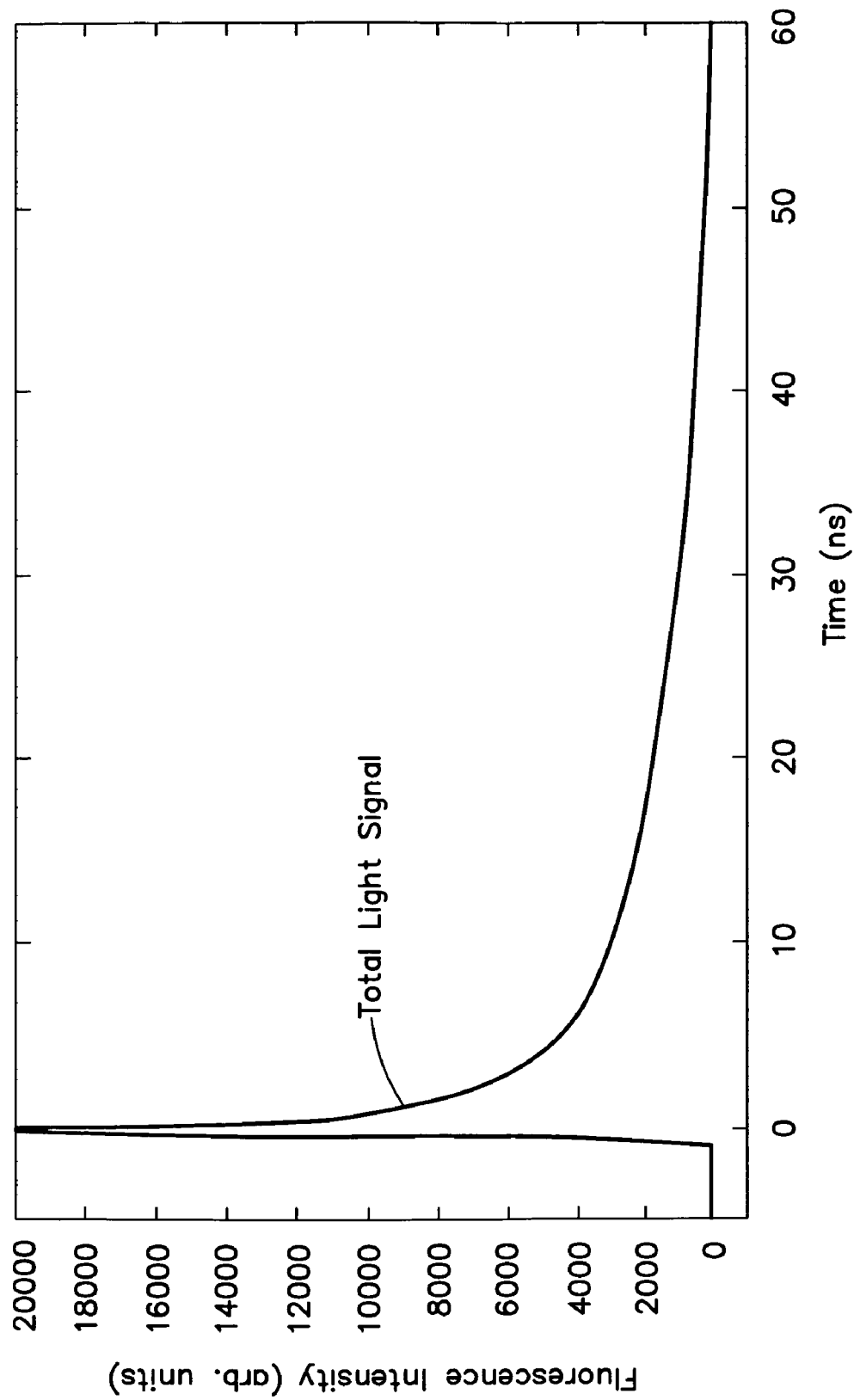
FIG. 1 is a graph showing a response, exemplarily shown as a composite emission decay profile, from an aerosol particle in accordance with one or more embodiments of the present invention.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Figure 2:
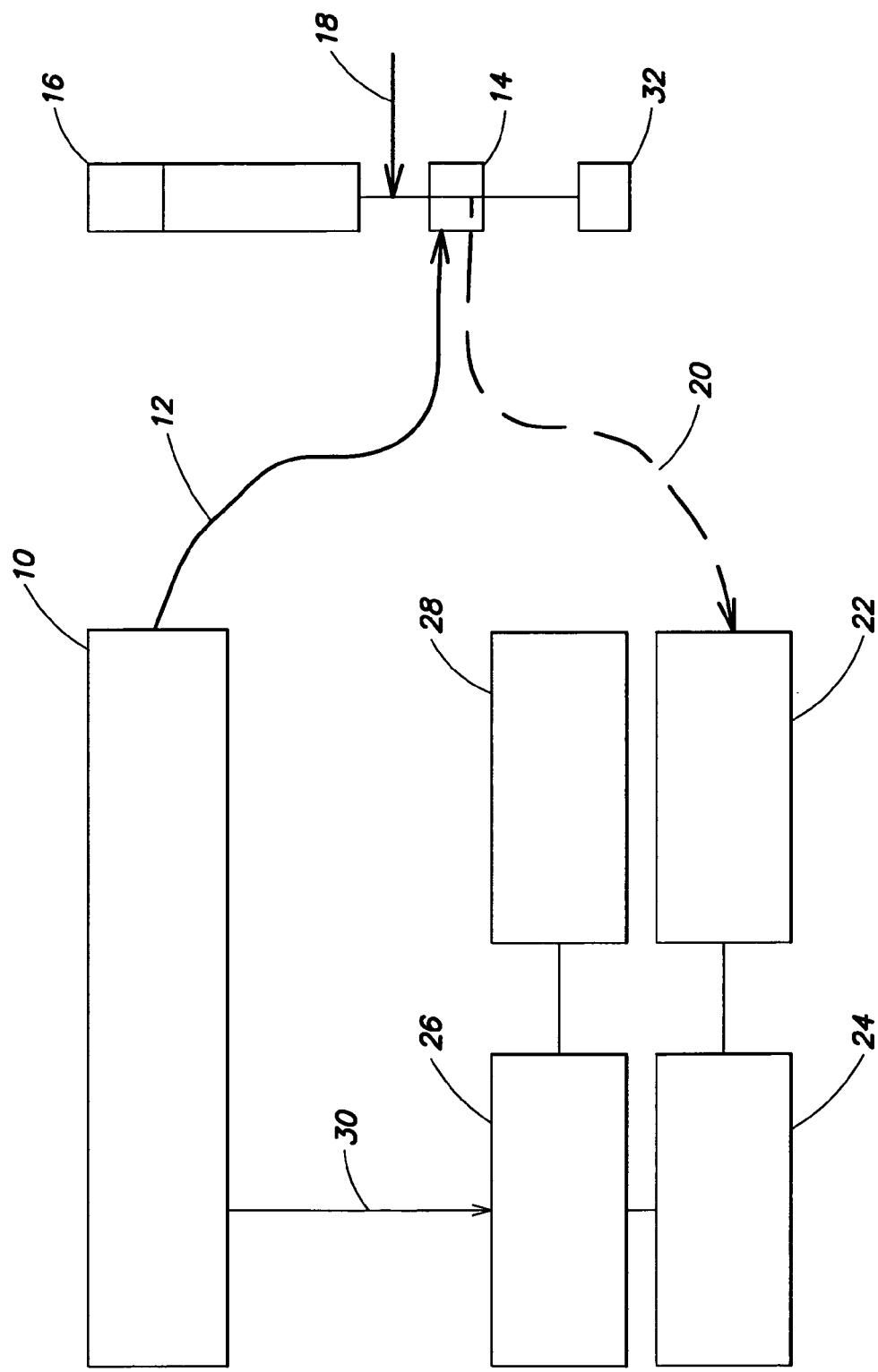
FIG. 2 is a schematic diagram showing a system in accordance with one or more embodiments of the present invention.

Detectable fluorescent compounds include, for example, polycyclic aromatic hydrocarbons (PAHs). Typical sources of PAH species are combustion sources, including for example, internal combustion engines that utilize gasoline or diesel fuel. Such sources typically discharge PAH species on soot particles, which though small, can aggregate and grow to larger size. Some PAH species are semivolatile, and will partially evaporate into the gas phase and may re-condense on other particles. Thus, in some cases, non-fluorescent particles may become fluorescent, especially where significant concentrations of PAH species would be present. In some cases, fluorescence due to PAH condensation on non-fluorescent particles may equal or exceed that from similarly-sized biological aerosol particles. Such PAH-contaminated particles can create false conditions. For example, the detecting instrument may register a false positive when non-biological species are present; or high levels of fluorescence from non-biological species may mask fluorescence from biological species, causing a false negative. Biological molecules have typically short fluorescence lifetimes, about less than 1 to about 7 ns. In contrast, PAH species have typically much longer lifetimes, typically exceeding 7 ns, and in some cases, from 10 ns to hundreds of nanoseconds.

Biological aerosol particles can be excited to produce fluorescence from biological fluorophores such as tryptophan, tyrosine, NADH, and/or flavin compounds, which would typically be present in such bioaerosol particles. In some cases, such particles can also scatter radiation as a scattered light pulse. Said excitation event can produce a signal pulse, typically a composite emission decay profile or composite intensity, exemplarily shown in FIG. 1. The composite emission decay profile typically includes a scatter component and fluorescence from one or more of particle-bound biological fluorophores; particle-bound, non-biological organic fluorophores; and, in some cases, gas phase, non-biological organic fluorophores present.

The systems and techniques of the present invention can be characterized as discriminating between biological fluorescence and background pollution fluorescence, such as non-biological fluorescence.

In accordance with one or more embodiments, the present invention provides a method and system that employs the time emission decay profile, or fluorescence lifetime, to discriminate or characterize a sample of aerosol particles, in some cases or preferably, without the need for fluorescence wavelength information.

The systems and techniques of the invention can be characterized as providing a time resolved integrated laser induced fluorescence technique. For example and in accordance with one or more embodiments, the invention can provide a system and a method for using time-resolved light detection to discriminate between classes of fluorescing molecules to detect and, in some cases, count biological aerosol particles. The methods and systems of the present invention can classify sources of light according to arrival time at the detector. For example, very fast-arriving light, typically arriving less than about 0.1 nanoseconds (ns) relative to, typically the center, of an initiating emission, such as a laser pulse, can be classified as scattered light; fast-arriving light, typically arriving less than about 1 ns to about 7 ns, can be classified as having a biological fluorescence origin; and slow-arriving light, typically arriving greater than 7 ns, can be classified as fluorescence of a non-biological nature or origin. In some cases, because the processes can begin simultaneously, some of the scattered light can be fast fluorescence in nature and some of the fast fluorescence can be slow fluorescence. Accordingly, the systems and techniques of the present invention can correct for any overlap between such categories.

The present invention can be directed to tiered biological aerosol particle detection systems. For example, a first tier can comprise a fast, sensitive cue detector that typically operates, preferably continuously, to detect suspicious events. When such an event is detected, the fast detector typically cues a highly specific identification detector or detector array. Such a configuration can reduce false alarms without the expense and maintenance burden typically associated with continuously operating the specific identification detector. Thus, in accordance with one or more embodiments, the present invention can utilize time resolved induced fluorescence techniques to detect suspicious events and cue one or more specific identification detectors.

In accordance with one or more embodiments, the systems and techniques of the present invention can detect natural, induced or resultant emissions, such as reflections or fluorescence of a sample comprising bioaerosol particles and resolve or deconvolve a response such as a composite time-dependent intensity into any one of a scatter component, non-biological component, and biological component. The measured intensity can be resolved into one or more non-biological components and, in some cases, one or more biological components.

The measurable emission can result naturally or be induced by an energy source. For example, aerosol particles can be excited to emit fluorescence by one or more electromagnetic radiation systems. The energy source can emit excitation energy in one or a spectrum of wavelengths. In accordance with one or more embodiments, the energy source 10 of the system of the present invention can comprise one or more electromagnetic radiation sources such as, but not limited to one or more lasers, as exemplarily shown in FIG. 2. Preferably, the excitation device, such as laser 10, can emit radiation, shown being transmitted through one or more optical fibers 12, with a pulse width sufficiently small that the scattering signal decay can be distinguished from a 1 ns emission decay profile. For example, a suitable pulse width can be less than about 5 ns and is preferably less than about 500 ps. The responses, such as a composite emission decay profile, typically scattered and/or emitted energy from the particles can be directed through one or more optical fibers 20 to devices to amplify and/or convert the response to one or more analyzable signals. For example, the response can be directed to a monochromator 22, a photomultiplier 24, and/or and oscilloscope 26. The signal can then be analyzed by, for example deconvolution, to identify components thereof in, for example computer 28. Computer 28 can further analyze the deconvolved signal into a discriminant vector, which can be mapped to provide a characterization of the biological/non-biological nature of the particles. The system can further comprise filter 32 to reduce any scatter component. As used herein, the term "discriminant vector" refers to the deconvolved or derived components of a response from an excited particle. Typically each particle has an associated discriminant vector which can be compared by, for example, mapping to provide a characterization of the nature of the particle. For example, the discriminant vector can be mapped to provide an indication of a biological and/or non-biological aspect of the particle.

Optionally, a trigger signal 30 can be directed to, for example oscilloscope 26, to provide an index for initiation of analysis sequences.

The laser light may interact with particles in a defined region of space and observed and/or a parameter thereof measured by a detector. The interaction region can be enclosed in a flow cell 14, which can prevent unwanted ambient particles and unwanted ambient light from contamination or otherwise introducing unquantifiable interferences. Particles to be analyzed, from source 16, can be introduced into flow cell 14 through a small nozzle, to confine them to a well-defined interaction region where the excitation energy, such as a laser light, can be concentrated, and where the detection optics or optical devices can focus, for efficient collection of emissions. Preferably, the particle stream is accompanied, more preferably, surrounded with an annular flow of particle-free air, which is typically referred to as sheath air 18. Sheath air 18 can further collimate the particle stream so that it can be confined in the interaction region and can prevent particle deposition on the optics of the system. More preferably, annular flows of the particle stream and the sheath air are combined or flow isokinetically, with the same velocity, to reduce any turbulent mixing that may cause particles to be transported from the inner flow to the outer flow. Concave mirrors, spherical, parabolic, or elliptical, can be further utilized to reflect emitted energy, e.g., light, traveling away from the collection optics, so that it can travel toward and be captured by the collection optics.

Figure 3:
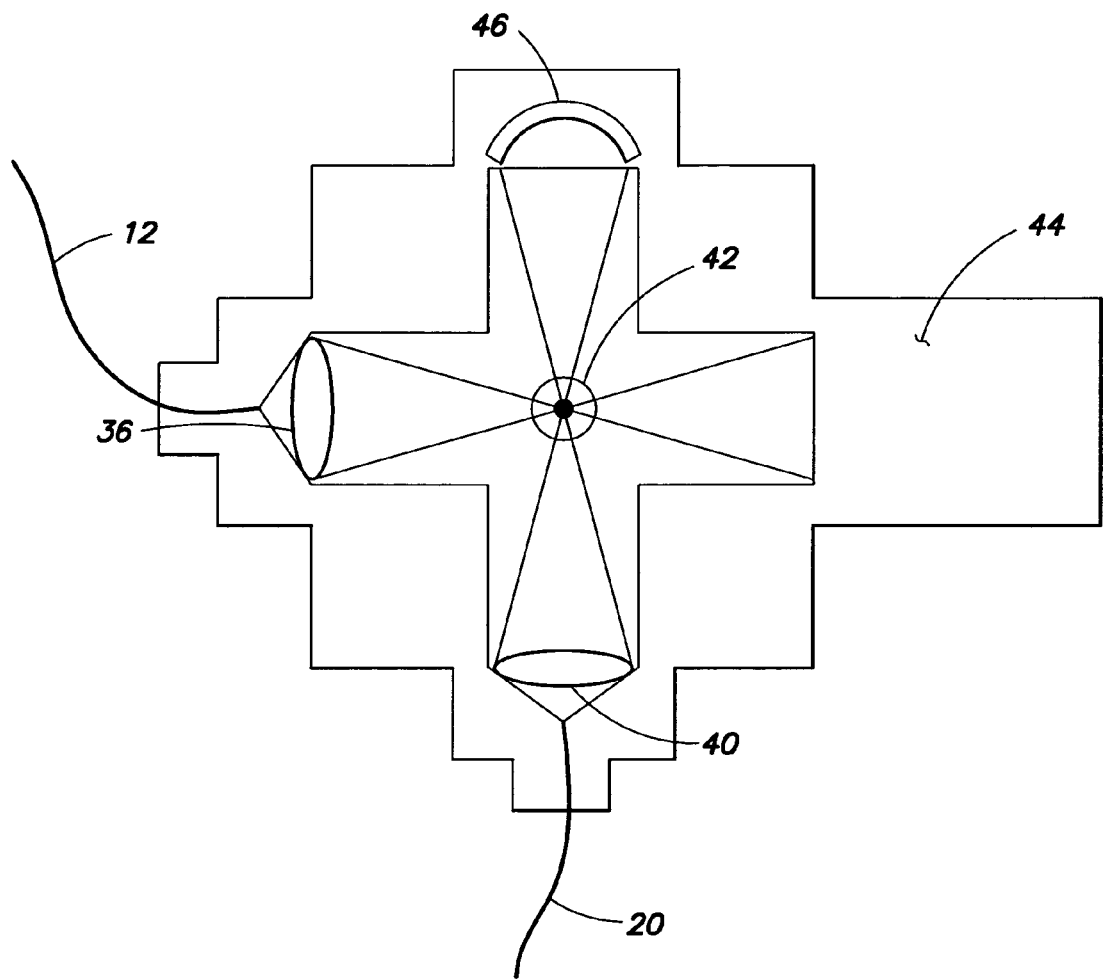
FIG. 3 is a schematic diagram of a flow cell utilizable in accordance with one or more embodiments of the present invention.

As shown schematically in FIG. 3, flow cell 14 can have one or more excitation focusing devices such as focusing lens 36 that can direct the energy directed through fiber 12 to a particular desired region 42 to increase the likelihood of interaction with the particle or particles under analysis. Flow cell 14 can further comprise one or more collection systems such as collection lens 40 that directs emitted response energy, e.g. composite emission decay profile, to fiber 20. Flow cell 14 can further comprise a beam dump 44, typically disposed distant from focusing lens 36, to capture energy not absorbed or scattered. Further, flow cell 14 can comprise one or more retroreflectors 46 to facilitate direction of a response to collection lens 40.

Examples of suitable excitation devices include a SURELITE™ I quadrupled YAG laser with a laser emission at 266 nm, available from Continuum, Santa Clara, Calif., a quadrupled YAG microchip laser with a laser emission at 266 nm, available from JDS Uniphase Corporation, San Jose, Calif.; a nitrogen laser with an emission at 315 nm; a modulated diode laser system with a laser emission at 375 or 405 nm, available from Becker & Hickl GmbH, Berlin, Germany; and a tripled Ti:Sapphire laser with tunable output in the ultraviolet regime.

In accordance with one or more embodiments, the systems and techniques of the present invention can comprise or utilize a suitable flow cell for detection of emitted light from an aerosol sample. The flow cell may comprise, for example, an enclosed space formed by the intersection of three tubes or boreholes or channels, preferably, along three orthogonal axes. The excitation energy can be introduced along one axis by, for example, suitable optics or optical devices so that it can be concentrated in the interaction region. The detection optics can be placed along the second axis so that the emitted energy can be transmitted or reflected into one or more detectors. A concave retroreflector may be placed opposite the detector to increase the light collection efficiency, preferably when a single detector is utilized. The airstream containing the particles, and optionally an annular flow of particle-free sheath air, can be introduced isokinetically along the third axis.

Any suitable detector can be utilized in the systems and techniques of the present invention to measure a composite emission decay profile. The detector can measure a specific wavelength, a portion of the emitted spectrum, or, in some cases, the entire measurable spectrum. The detector should have a suitably rapid response time, for example less than 5 nanoseconds or preferably less than 500 picoseconds. Examples of suitable detectors include a model 1P28 photomultiplier tube, available from Hamamatsu Photonics, K.K., Hamamatsu City, Japan; a model APM-400 avalanche photodiode module available from Becker & Hickl GmbH, a model PMC- 100 photomultiplier module also available from Becker & Hickl GmbH; and a streak camera available from Hamamatsu Photonics, K.K.

In accordance with one or more embodiments of the invention, the signal representing the composite emission decay profile can be obtained by a spectroscopic method preferably having time resolution, such as 100 picoseconds (ps) to distinguish different components of the decay. For example, a time-correlated single photon counting (TCSPC) technique may be utilized or other techniques that record low level light signals with, preferably, picosecond time resolution.

The signal, typically corresponding to a measured response to the initiating or exciting energy can be represented as a signal, which can be sent to one or more analytical devices or system. Suitable devices or system components include a digitizing oscilloscope with minimum bandwidth 500 MHz such as a model TDS 3052 oscilloscope available from Tektronix, Inc., Beaverton, Oreg.; a computer interface card, such as a general purposed interface board (GPIB), USB, or RS-232 interface; a computer preferably utilizing a PENTIUM®-based microcomputer or a "palmtop" or personal digital assistant computer; instrument control systems such as MATLAB,™ IGOR PRO,™ LABVIEW,™ or other custom software and/or hardware; and waveform analysis such as MATLAB,™ IGOR PRO,™ SIGMAPLOT,™ or other custom software or hardware. The analytical device can evaluate the signal and decompose it into substituent components. Preferably, the device can utilize one or more decomposition techniques to identify a scatter component and, if present, a fluorescence component. More preferably, the device can also utilize techniques such as deconvolution to identify a non-biological component, and, if applicable, a biological component, of the composite response or the fluorescence component thereof. In some cases, the response can comprise one or more scatter components and/or one or more fluorescence components. In still other cases, the fluorescence component can comprise one or more biologically-corresponding or biological component and one or more nonbiologically-corresponding or non-biological component. The deconvolution techniques can be performed until derived results have sufficiently converged compared to the measured signal. Such convergence criteria can be tailored to particular requirements.

Figure 4:
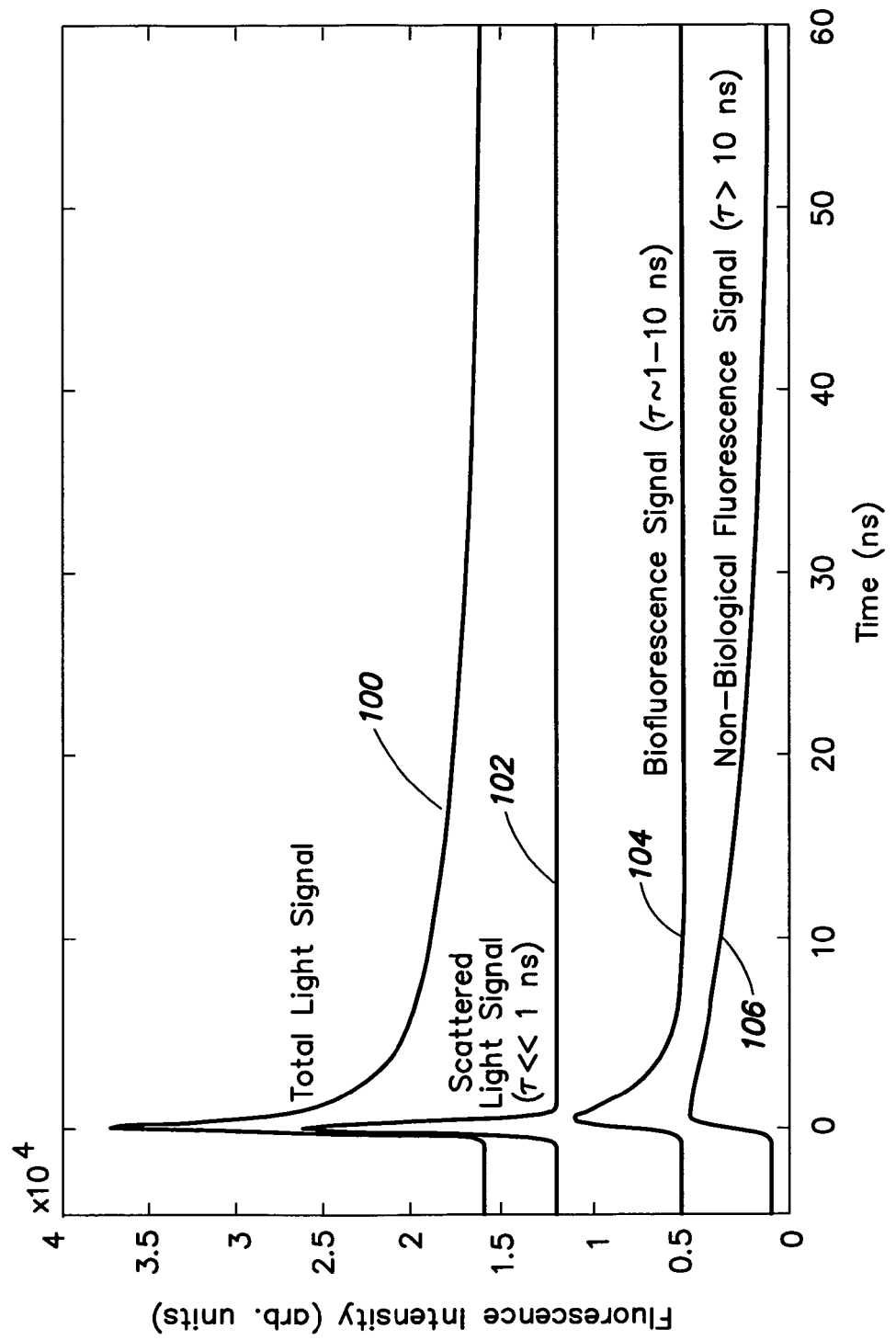
FIG. 4 is a graph showing components of the decay shown in FIG. 1.

Signal decomposition techniques can be used to deconvolute the signal to obtain very fast, fast, and slow decays, each typically characterized by decay constants on the order of picoseconds, nanoseconds, and tens of nanoseconds, respectively. FIG. 4 shows deconvolved components from the total or composite response measured as a composite emission decay profile in FIG. 1. FIG. 4 exemplarily shows a total response signal 100 comprising a scatter component 102, typically associated with an exciting energy, and can be considered reflected, scattered energy from, for example, illuminated particles. In FIG. 4, the scatter component is shown with a Gaussian profile that may arise from the time profile of the excitation energy, e.g. the laser pulse. However, the scatter component will typically have the profile of the Instrument Response Function, discussed further below. The response can further comprise a biological component 104, typically having an exponential emission decay profile and a non-biological component 106, also typically having an exponential emission decay profile. As described, the non-biological component typically has a longer duration profile relative to the biological component. By separating the signal components according to their decay characteristics, the biological fluorescence can be distinguished from non-biological fluorescence and from scattered light. Thus, the present invention can provide systems and techniques that utilize signals that can be recorded with a single photodetector, without dispersion or filtering, e.g. by wavelength, of the signal.

However, a filter may be utilized, at the excitation wavelength, to reduce the scattered light intensity component, which can be advantageous because the scatter component typically has a greater magnitude than the magnitude or contribution attributable to biological and/or non-biological fluorescence. The filter may comprise a long-pass or band-pass filter, which, preferably, selectively compensates for the excitation wavelength.

The composite intensity decay profile can be characterized as a sum of terms including S, the scattered light pulse, and n fluorescence decay terms $I_n$. The scattered light pulse profile is typically influenced by the distribution of ray lengths from the excitation source to the detector, and may be considered sufficiently narrow that it may be assumed to have zero width, relative to elapsed time. Intensity decays can be represented as $I_n = I_{o,n} e^{-(t/\tau n)}$. Additionally, each term is typically convolved with the Instrument Response Function (IRF), which arises from the laser pulse shape and other aspects of the optical system and detector electronics. The IRF is determined via reflected or scattered light, where it is assumed that the only contribution the shape of a reflected or scattered light pulse is the IRF. This determined IRF is typically used during the deconvolution process.

A time constant $\tau_n$ can be respectively associated with each of the n biological and non-biological fluorescence decay components. Notably, one or more time constants, corresponding to one or more exponential profiles, can comprise each of the biological and the non-biological components.

Deconvolution of the different decays allows the fluorescence to be grouped into short and long lifetime bins or subcomponents. As exemplarily shown in FIG. 4, more than half of the total fluorescence (area under the curve) detected between about 1 ns to about 7 ns can be due to non-biological sources, such as PAH compounds, in the gas phase and/or adsorbed on bioaerosol particles. Deconvolution can be performed by utilizing statistical curve-fitting techniques to identify the scattering component, the non-biological component and the biological component. These statistical techniques typically construct a trial composite decay profile using initial guesses for the intensity and decay parameters. Initial guesses are based on physical expectations about the sample being characterized. The parameters are typically varied to minimize the difference between the constructed composite decay profile and the composite decay profile. The vector of parameters that reduces the difference between constructed and measured profiles below some predetermined tolerance, usually within a predetermined maximum elapsed time, is chosen as best representing the components of the measured composite decay profile. An example of a suitable algorithm for curve-fitting is the Levenberg-Marquardt method. Examples of software containing the Levenberg-Marquardt algorithm or other suitable curve-fitting algorithms include, but are not limited to, IGOR PRO,™ SIGMAPLOT,™ MATLAB,™ and FLUOFIT™ as disclosed by, for example, J. Enderlein and R. Erdmann in "Fast Fitting of multi-exponential decay curves", Optics Communications 134(1–6), 1997, pp. 371–378.

The intensities corresponding to the scatter, total biological fluorescence, and total non-biological fluorescence may be determined by summing all intensities for components with lifetimes within a certain range. For example, biological fluorescence could be taken as the sum of all intensities for components with lifetimes between about 0.1 and about 7 ns. Likewise, non-biological fluorescence could be taken as the sum of all intensities for components with lifetimes greater than about 7 ns. However, the lifetime ranges used to classify emission as scatter, biological fluorescence, or non-biological fluorescence may be chosen based on one or more factors including physical insights about the system being measured, lifetimes published in the scientific literature, and laboratory measurements of test particles. In some cases, the classification separation between biological and non-biological fluorescence can be varied as necessary to accommodate region or environment specific requirements. Thus, the biological components can be classified as those having time constants between about 0.1 ns to about 7 ns and, correspondingly, non-biological components can be classified as those having time constants greater than about 7 ns.

The total scatter and fluorescence intensities can thus define a discriminating vector comprising n-dimensional components corresponding to one or more of the scatter component, the biological components, and the non-biological components. Typically, the discriminating vector provides a characterization of the nature of the sampled aerosol particles in a three-dimensional map.

In some embodiments of the invention, the fluorescence intensities can be normalized by dividing by the scatter value. This can reduce the number of vector components by a degree of freedom to, for example, two, so a two-dimensional map can be used to provide a characterization of the nature of the analyzed sample of aerosol particles.

Figure 5:
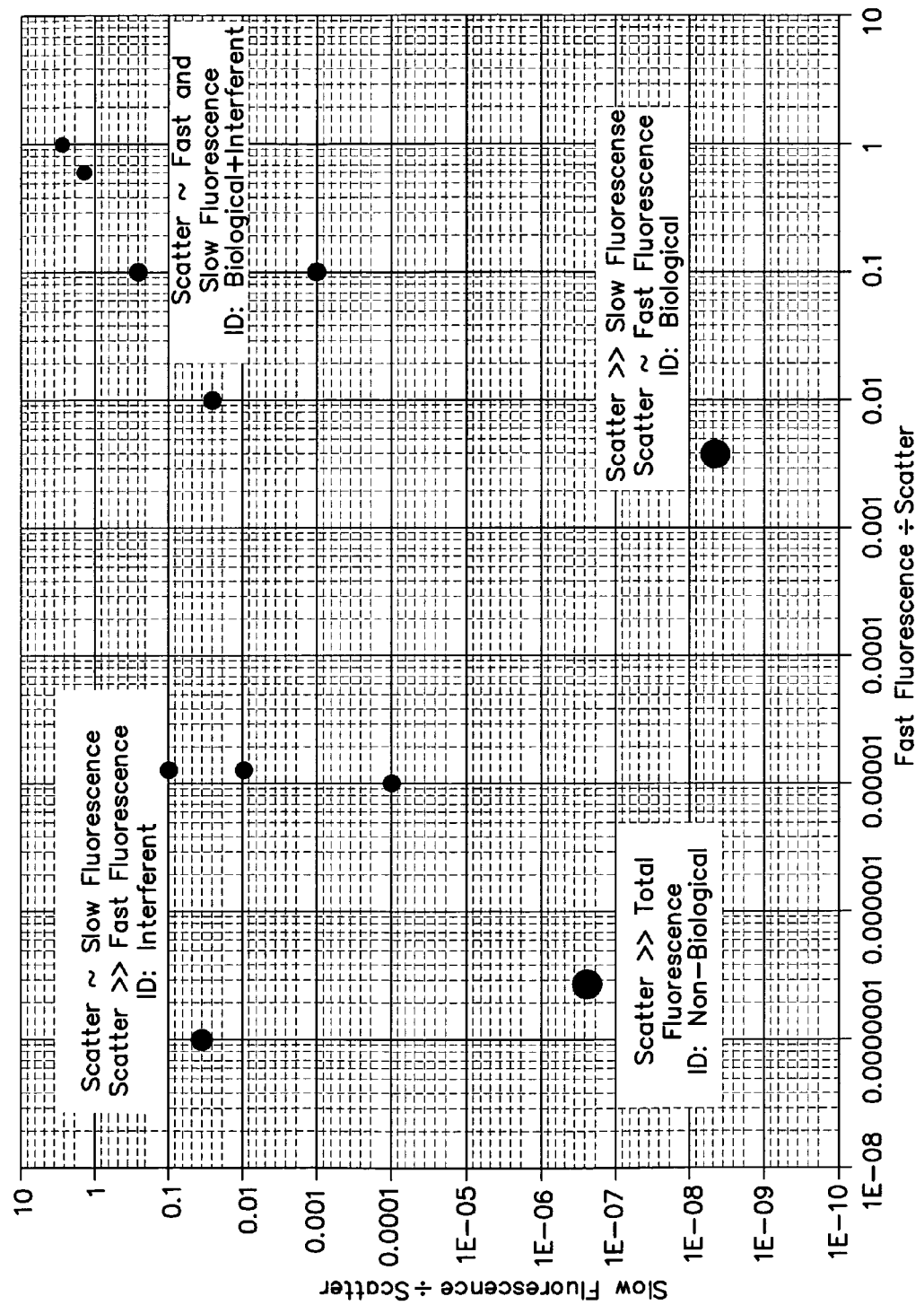
FIG. 5 is map characterizing deconvolved results in accordance with one or more embodiments of the present invention.

For example, once the decay rates of the different signal components have been characterized, the corresponding, associated initial response values may be plotted on a map that aids in discriminating between biological and non-biological signatures. FIG. 5 shows an example of where various aerosol types may be found on a map comparing normalized fluorescence intensities and scattering intensity. As exemplarily shown in FIG. 5, toward the right side of the map, the fast intensity component, typically associated with biological fluorescence can be equal to or greater than the slow intensity, which indicates that biological species are probably present. In some cases, scattering intensity can be represented by the size of the spot; if large, it can indicate a large particle size. Scatter intensity may be used, as is done with, for example, BAWS Tier III, as a proxy for size, so that intense fluorescent scattering species are probably large pollen grains, while very weak fluorescent scattering species may be submicron soot aerosols or fragments of bioparticles. Measurements of known aerosol types may be utilized to populate such maps and, preferably, provide delineating boundaries between biological and non-biological aerosols.

Other methods of analyzing the data to produce classification criteria can be utilized in accordance with the systems and techniques of the present invention. For example, Fourier transformation of the time domain data can yield a spectrum of decay frequencies that can be associated with the decay times. It is also possible to characterize particles based on the ratio of non-biological fluorescence to biological fluorescence, with or without normalization to scattering. Further, maps similar to that presented in FIG. 5 may be generated for other classification criteria, see for example FIG. 8, which is discussed in the examples.

In some cases, it is possible to combine the time-resolved detection method with other techniques such as those pertinent to dispersed or filtered fluorescence, to obtain both time and spectral information about the measured response. This can yield additional information about the fluorescing species or molecules. For example, the manner by which the fluorescence spectrum changes over time may indicate spectral relaxation, which can be indicative of how quickly a molecule's environment adapts to photonically induced changes in the molecule's electric field. Spectral relaxation can be dependent on the viscosity and polarity of the molecule's environment; thus, it may be a way of differentiating a molecule adsorbed on a solid surface, from a molecule embedded in a biological membrane, from a molecule in a liquid environment, e.g. cellular cytoplasm. This may allow detailed identification of classes of biological agents, because, it is believed, bacterial spores typically have little or lower water relative content.

Aerosol particles, entrained in airflow, can be excited, for example, one at a time, by pulsed laser radiation, light, at a wavelength that produces fluorescence from biological fluorophores such as tryptophan, tyrosine, NADH, or flavin compounds. Said particles also scatter said radiation to produce a scattered light pulse. Both fluorescence and scattered light can be detected by the same detector. This produces a signal pulse similar to that shown in FIG. 4. The measured signal corresponding to a response can comprise scattered light components and one or more of particle-bound biological fluorophore components and particle-bound, non-biological organic fluorophore components, and, in some cases, gas phase, non-biological organic fluorophore components, in the excited or illuminated focal region.

In accordance with one or more embodiments of the invention, the signal can be obtained by sampling at predetermined and/or strategic intervals using, for example, a spectroscopic method to distinguish different components of the decay. For example, a suitable method can comprise time-gated photon counting, but other methods may also be suitable.

Preferably, the excitation energy, e.g. laser beam, has a pulse width sufficiently small that the scattering signal decay can be distinguished from a 1 ns emission decay profile. A suitable pulse width can be about less than about 500 ps.

Figure 6:
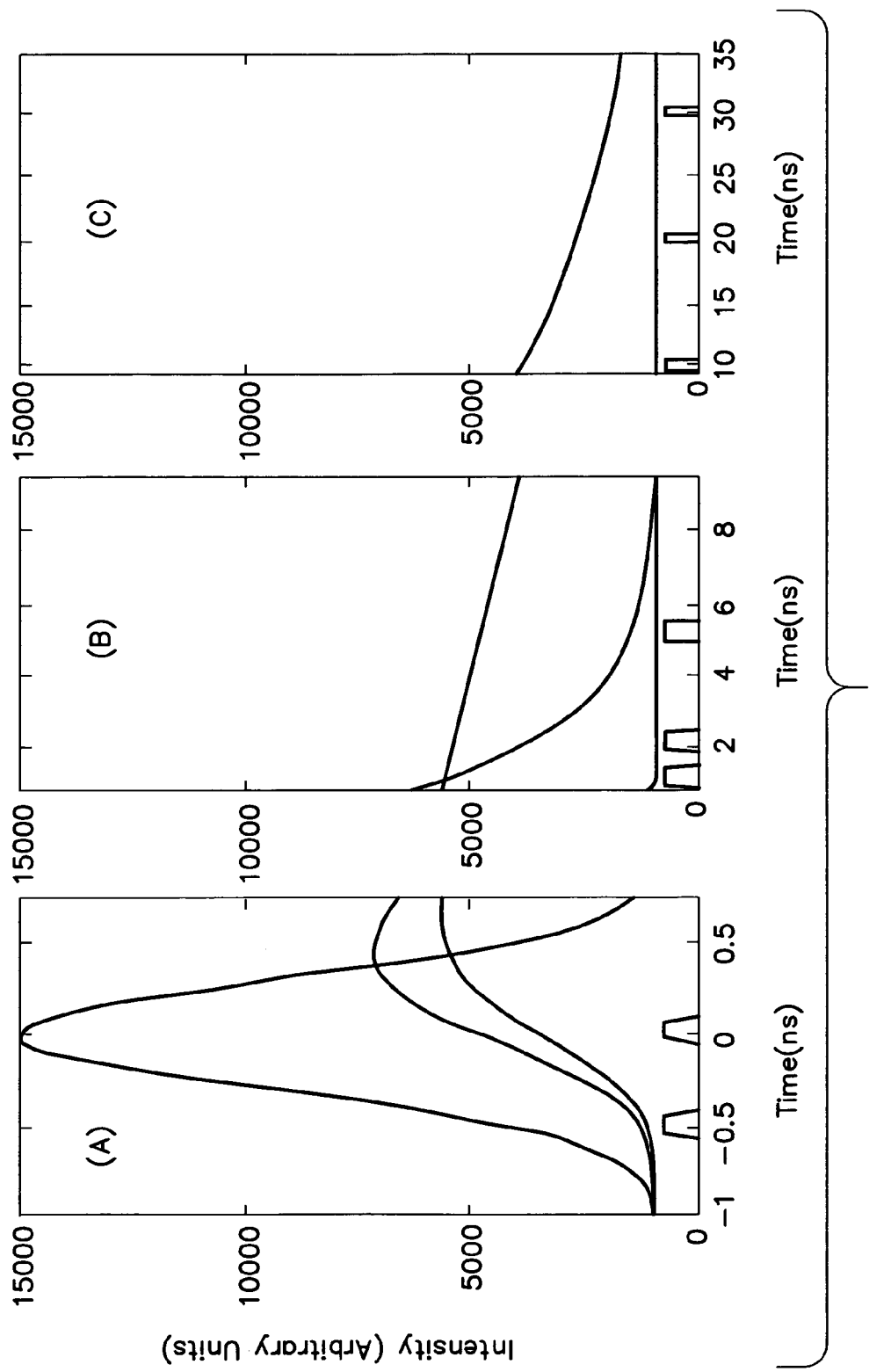
FIG. 6 is a graph showing the relative nature of a scatter component (A), a biological fluorescence component (B), and a non-biological fluorescence component (C) of a typical decay response.

The gate start times and gate widths are chosen to sample the light intensity at times when most of the light is due to one source or another. FIG. 6 shows how gate times can be selected. The signals can be considered to be corresponding components exemplarily shown in FIG. 4, labeled as very fast scatter component 102, fast biological fluorescence component 104, and slow non-biological fluorescence component 106. As exemplarily shown, the signal traces can be offset from zero for clarity. The gate pulse is shown in the bottom trace, where a high gate signal corresponds to a period during which the detector is on or activated, and a low value corresponds to a period during which the detector is off or inactive. FIG. 6 exemplarily shows three panes to indicate events occurring on different time scales. For example, in (C), the gates, set at about 10 ns, 20 ns, and 30 ns, receive response measurements associated with long-lived, typically non-biological, fluorescence. Fluorescence intensities at such points may thus be used to estimate the contribution from non-biological fluorescence. In (B), gates, set at about 1 ns, 2 ns, and 5 ns, receive response measurements can be associated with long-lived fluorescence, which would prefer ably be subtracted based on the preceding analysis pertinent to long-lived, typically non-biological, fluorescence, and/or short-lived, typically biological, fluorescence. In (A) at a time from about −0.5 ns to about 0 ns, after compensating for estimated fluorescence, as determined above, the remaining detected light can be attributed to scattering of the exciting energy, e.g., the laser. Gate activation periods can be relative to the center of an excitation energy discharge but can be measured relative to the trigger that initiates the excitation energy discharge. Gate positions can be optimized based on data from environmental and test aerosols.

The three measured categories can then be used to map the data as shown in FIG. 5. Likewise, the position on the plot can be indicative of the nature of the sampled aerosol particles, e.g., whether the fluorescence is biological, non-biological, or both. Other mapping techniques can utilize ratios of short and long lifetime fluorescence components relative to the scatter component and provide a two-dimensional map as well as computing the ratio of short-lifetime fluorescence to long-lifetime fluorescence and plotting the ratio relative to scatter to also provide a two-dimensional characterization of the nature of the particles. Further, statistical and/or geometric techniques can be utilized to, for example, assign probabilities as to the nature or likelihood of biological or non-biological character of the particles. For example, statistical techniques can be utilized to assign a probability or likelihood that the particle is or comprises a target microorganism. Likewise, geometrical techniques can be utilized to assign distances representative of the character of the particle relative to one or more categories. For example, separation distances can be determined for a measured, analyzed discriminant vector relative to vectors of one or more known particles. The relative separations can thus be viewed as a likelihood of presence, likelihood of result, and/or likelihood of contribution.

The functions and advantages of these and other embodiments of the invention can be further understood from the examples below. The following examples illustrate the benefits and advantages of the systems and techniques of the invention but do not exemplify the full scope of the invention.

EXAMPLE 1

Prophetic Characterization System

Prophetic data can be generated for several types of particles; non-fluorescent particles (scattered light only); particles containing a mixture of common atmospheric PAHs having representative lifetimes about 15, about 22, and about 30 ns; hazardous bioaerosols (respirable bioparticles) having a representative lifetime of about 2 ns; background bioaerosols (e.g., a pollen grain) having a typical lifetime of about 2 ns.

This prophetic example data is constructed to approximate the results expected from one example implementation of the present invention. The experimental system can comprise a quadrupled SURELITE I™ YAG laser emitting at 266 nm available from Continuum, Inc., and a flow cell comprising about two-inch cubic aluminum block bored through on three orthogonal axes. Aerosol particles are introduced isokinetically within an annular, particle-free sheath flow, wherein the aerosols interact with the emitted laser energy in a central interaction region. Emitted radiation from the sample of aerosol particles or reflected by a retroreflector is collected by a collection optical system. Excess laser light that is not absorbed or scattered by the sample of aerosol particles is captured by a beam dump disposed distant from a laser focusing lens. A silica/silica optical fiber cable conducts the emitted laser energy to the cell and a second silica/silica optical fiber conducts the response from the cell to the detector, both optical fibers are model FVA available from Polymicro Technologies, LLC, Phoenix, Ariz. Optionally a monochromator, such as those available from Jarrell Ash Corp./Thermo Electron Corp., Woburn, Mass., or other similar device can be utilized to select a single emission wavelength for detection. The system can further comprise one or more photomultiplier modules such as a model 1P28 photomultiplier tube available from Hamamatsu Photonics, K.K., Hamamatsu City, Japan; a model TDS 5032 digitizing oscilloscope available from Tektronix, Inc., Beaverton, Oreg., to enhance or amplify the response; a computer comprising a PENTIUM® microprocessor with a general purpose interface board (GPIB) running LABVIEW™ software, available from National Instruments Corporation, Austin, Tex., to control the system and/or record and analyze data. Data analysis can be performed utilizing commercially or otherwise freely available software from for example MATLAB™ available from MathWorks, Inc., Natick, Mass. and/or FLUOFIT™ software for deconvolving composite emission decay profiles by performing, for example, multi-exponential least squares fitting.

The specific hardware configuration chosen to make the fluorescence measurements determines the Instrument Response Function (IRF). The IRF is a temporal function that alters the expected exponential decay profiles in a manner equivalent to mathematical convolution. Therefore, if the IRF for a given experimental configuration is known, it is possible to predict the approximate form of the signal that will be recorded from a particle of specified size and composition.

Further, the IRF for a given experimental configuration can be recorded by measuring the time-dependent intensity profile of a light pulse reflected from a mirror or any convenient, non-fluorescing surface. Therefore, it is possible to construct a prophetic data set relating to a particle of specified size and composition, as measured by a spectrometer of specified hardware configuration. The basic component of a time-domain fluorescence signal is an exponential decay, $Ie^{(-t/\tau)}$, where I is the intensity and t, the fluorescence lifetime. Individual signals for scattered light, and fluorescence with lifetimes characteristic of biomolecules and common PAHs, are summed to construct the ideal decay profile. The recorded IRF for the spectrometer in use is convolved with the ideal decay profile to produce a prophetic decay profile for the specified particle and experimental system.

EXAMPLE 2

Analysis of a Prophetic Response

FLUOFIT™ software was used to analyze a convolved representative response to derive up to three exponential decay components and one scatter component. The resultant of this was a set of intensities and lifetimes that characterize different components of the decay. Intensities for short-lived fluorescence were summed and taken as representative of biofluorescence. Intensities for long-lived fluorescence were summed and taken as representative of PAH fluorescence. The IRF intensity was taken as representative of scattered light, which is typically related to particle size. The short- and long-lived fluorescence totals and scattered light total were used to locate the particle on a three-dimensional map to classify the various particles.

Table 1 lists exponential decay parameters of representative species that may be encountered. For PAHs, the "relative importance" (RI) is a measure of the importance with respect to fluorescence measurements, compared to biomolecules. The calculation was performed as follows: published measurements of concentration in atmospheric gas/particulate phase were used to estimate gas or surface concentration of the PAH in question. Particles sizes of 2 μm diameter were utilized. Fluorescence emitted by the PAH was calculated based on the above concentration, multiplied by the absorption cross section and fluorescence quantum yield. The total fluorescence emitted from a 2 μm *Bacillus globigii* (BG) spore was estimated based on measurements from several laboratories.

PAH fluorescence was normalized relative to BG spore fluorescence to give the RI score. Of the 39 compounds found in the atmosphere by one environmental study, only five have RI of 0.1 or more. Of these, all but two have lifetimes longer than expected for bioparticles.

Representative exponential decay parameters were determined. The values used in this prophetic dataset relate to the Relative Importances and Lifetimes (listed in Table 1) and are listed in Table 2.

Five particle signals were constructed and listed in Table 3. The first particle representation corresponds to a dust grain having no fluorescence aspect. The second particle representation corresponds to a 2 μm diameter particle having PAH #1, 2, and 3 aspects. The third particle representation corresponds to a 2 μm diameter spore having a fluorescence time constant of about 2 ns. The fourth particle representation corresponds to a 20 μm diameter pollen with a fluorescence time constant of about 2 ns. The fifth particle representation corresponds to a microbial spore contaminated with PAH 1 and 3.

TABLE 1

Known atmospheric gas phase or particulate fluorophores along with estimated time constants (presented as lifetimes) as well as their estimated importance relative to BG fluorescence.

| Aerosol Species | Relative Importance | Lifetime (ns) |
|---|---|---|
| Phenanthrene (gas phase) | 1.5 | 57.5 |
| Phenanthrene (particle) | 1.5 | 57.5 |
| B. Globigii (2 μm dry spore) | 1.0 | 2 |
| Fluorene (particle phase) | 0.8 | 10 |
| Fluorene (air phase) | 0.6 | 10 |
| Naphthalene (particle phase) | 0.4 | 96 |
| C1-C4 Anthracenes (gas phase) | 0.4 | <6 |
| C1-C4 Anthracenes (particle phase) | 0.3 | <6 |
| Anthracene (particle phase) | 0.1 | <6 |

TABLE 2

Representative model fluorophores and scattering sources along with typical time constants (presented as lifetimes) and intensities in arbitrary units. These constituents were used to construct the prophetic example signals.

| Compound Name | Intensity (arbitrary units) | Tau, t (ns) |
|---|---|---|
| PAH #1 (phenanthrene) | 150 | 57.5 |
| PAH #2 (fluorine) | 80 | 10 |
| PAH #3 (C1-C4 anthracene) | 40 | 5 |
| Microbial Spore | 100 | 2 |
| Pollen Grain | 10,000 | 2 |
| Scatter from 2 um particle | 100 | 0 |
| Scatter from 20 um particle | 10,000 | 0 |
| Scatter from 100 um particle | 250,000 | 0 |

Figures 7A, 7B, 7C:
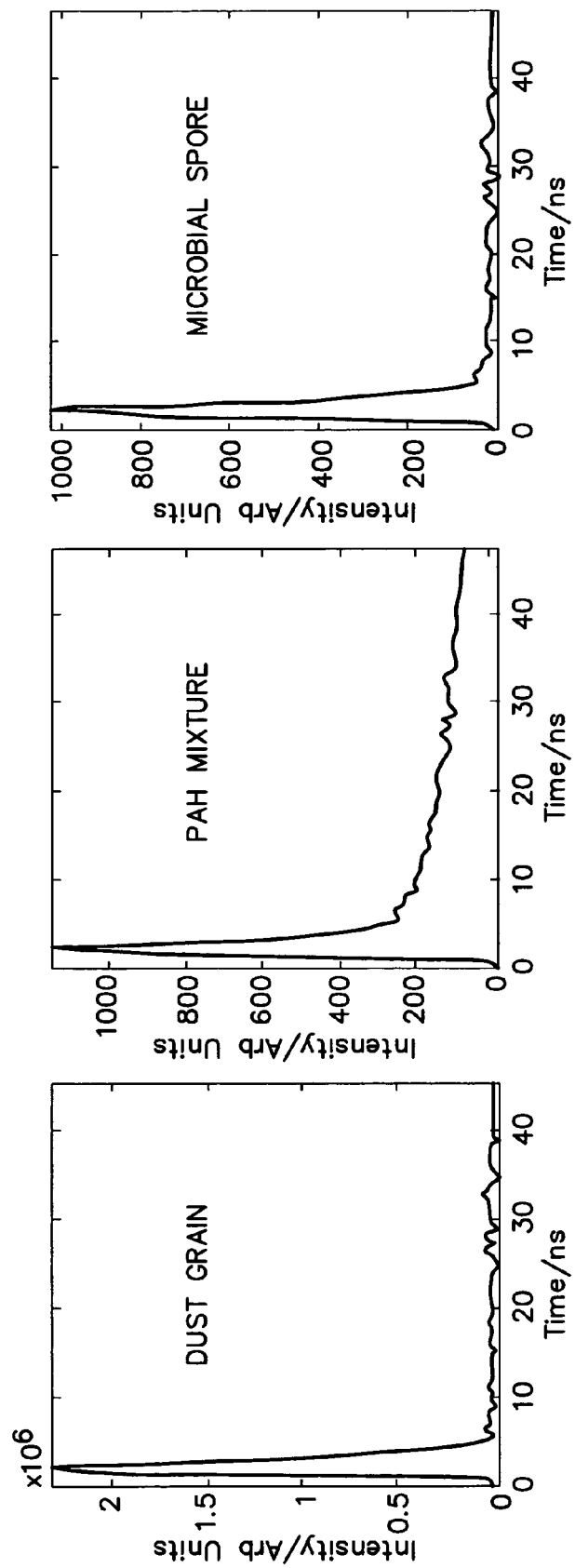
FIGS. 7A–7E are graphs showing constructed, prophetic decay responses for various particles as discussed in the examples.
Figure 7D:
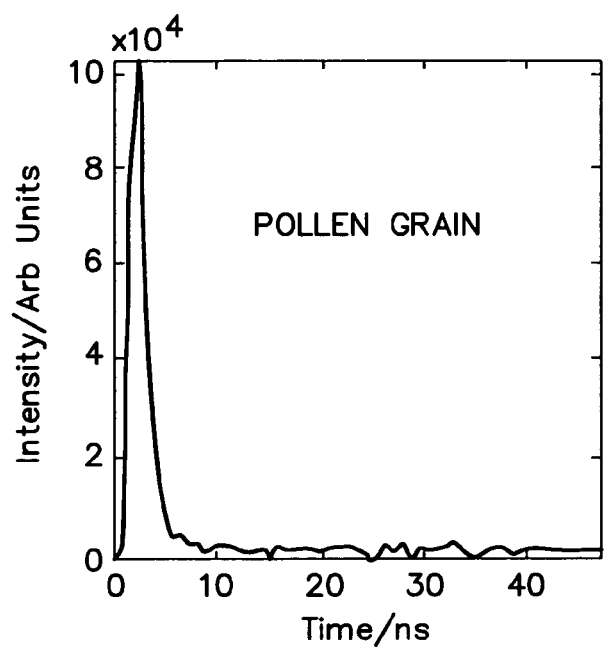
Figure 7E:
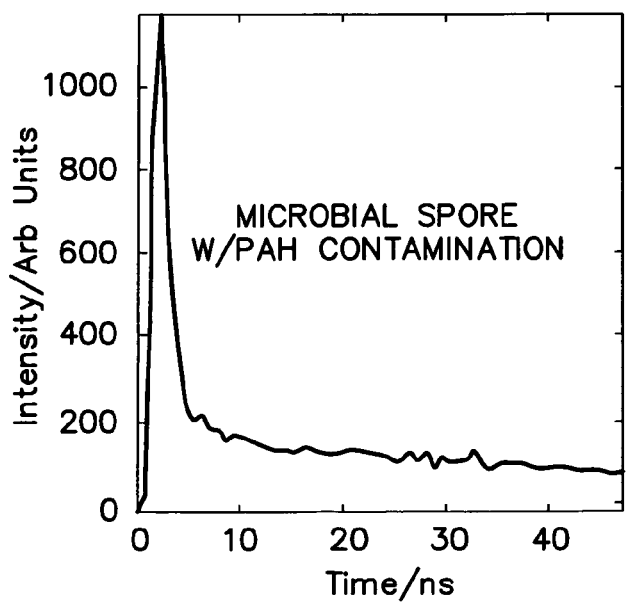

FIGS. 7A–7E show constructed decay profiles for each of these particles. FIG. 7A shows the constructed decay profile for the first particle, the dust grain. FIG. 7B shows the constructed decay profile for the second particle, a mixture of PAH 1, 2 and 3 on a 2 μm diameter particle. FIG. 7C shows the constructed decay profile for the third particle, microbial spore. FIG. 7D shows the constructed decay profile for the fourth particle, pollen. FIG. 7E shows the constructed decay profile for the fifth particle, spore with PAH 1 and 3 contaminations.

TABLE 3

Constructed particle description.

| Particle (Description) | Size (μm) Scatter Intensity | Fluorescent Intensity | Lifetimes (ns) |
|---|---|---|---|
| 1 (Non-fluorescent dust grain) | 100 2,500,000 | None | None |
| 2 (Mixture of PAH 1, 2 and 3) | 2 1,000 | 150, 80, 40 respectively | 57.5, 10, 5 respectively |
| 3 (Microbial Spore) | 2 1,000 | 100 | 2 |
| 4 (Pollen Grain) | 20 100,000 | 10,000 | 2 |
| 5 (Microbial/PAH 1 and 3) | 2 1,000 | 150, 40, 100 respectively | 57.5, 5, 2 respectively |

The decay profiles shown in FIGS. 7A–7E were deconvolved with multiexponential, least squares fit to derive intensity and lifetime of each decay component.

Table 4 lists the derived results. As shown in Table 4, for each of the constructed decay profiles, the derived Fit Percentage (which is representative of the initial intensity) closely corresponded to the Actual Percentage for each of the components of each particle. Likewise, the derived Fit Lifetime closely corresponded to Actual Lifetime. For example, for particle 1, which was a dust grain having a scatter component and no fluorescence component, the derived Fit Lifetime was about 0.003, indicative of no decay component, no fluorescence component.

For particle 3, the deconvolution process identified a scatter component and a fluorescence component, the fluorescence component classified as biological because it had a lifetime (Fit Lifetime) of less than about 7 ns. The scatter component was derived to be about 91% (as Fit Percentage), closely corresponding to the Actual Percentage (91%). The fluorescence component was derived to have a Fit Percentage (8.7%) close to the Actual Percentage (9%). The derived Fit Lifetime (1.5 ns) also corresponded closely to the Actual Lifetime (2 ns). Thus, the results presented in Table 4 show that various prophetically constructed particles can be characterized by, for example, deconvolution, to provide components of a response from the particle.

TABLE 4

Deconvolution results.

| Particle | Component | Actual Intensity | Actual Percentage | Actual Lifetime | Fit Percentage | Fit Lifetime | Intensity error | Lifetime Error |
|---|---|---|---|---|---|---|---|---|
| 1 | Scatter | 2,500,000 | 100 | 0 | 100 | 0.003 | 0 | 0.003 |
| 2 | Scatter | 1,000 | 79 | 0 | 88 | 0.04 | 9 | 0.04 |
|  | PAH #1 | 150 | 12 | 57.5 | 6.2 | 57.5 | −5.8 | 0 |
|  | PAH #2 | 80 | 6 | 10 | 3.9 | 9.86 | −2.1 | 0.14 |
|  | PAH #3 | 40 | 3 | 5 | 0 | 4.77 | −3 | 0.23 |
|  | Total |  | 1,270 |  |  |  |  |  |

TABLE 4-continued

Deconvolution results.

| Particle | Component | Actual Intensity | Actual Percentage | Actual Lifetime | Fit Percentage | Fit Lifetime | Intensity error | Lifetime Error |
|---|---|---|---|---|---|---|---|---|
| 3 | Scatter | 1,000 | 91 | 0 | 91.3 | 0.04 | 0.3 | 0.04 |
|   | Bio | 100 | 9 | 2 | 8.7 | 1.5 | −0.3 | 0.5 |
|   | Total | 1,100 | | | | | | |
| 4 | Scatter | 100,000 | 91 | 0 | 91.3 | 0.04 | 0.3 | 0.04 |
|   | bio | 10,000 | 9 | 2 | 8.7 | 1.5 | −0.3 | 0.5 |
|   | Total | 110,000 | | | | | | |
| 5 | Scatter | 1,000 | 78 | 0 | 86 | 0 | 8 | 0 |
|   | PAH #1 | 150 | 12 | 57.5 | 6 | 57.5 | −6 | 0 |
|   | PAH #3 | 40 | 3 | 5 | 2.2 | 4.9 | −0.8 | 0.1 |
|   | Bio | 100 | 8 | 2 | 5.9 | 1.95 | −2.1 | 0.05 |
|   |   | 1,290 | | | | | | |

EXAMPLE 3

Mapping Particle Characteristics

In this example, particle characteristics as represented by a discriminant vector were mapped according to their position in time-resolved fluorescence signal space.

Figure 8:
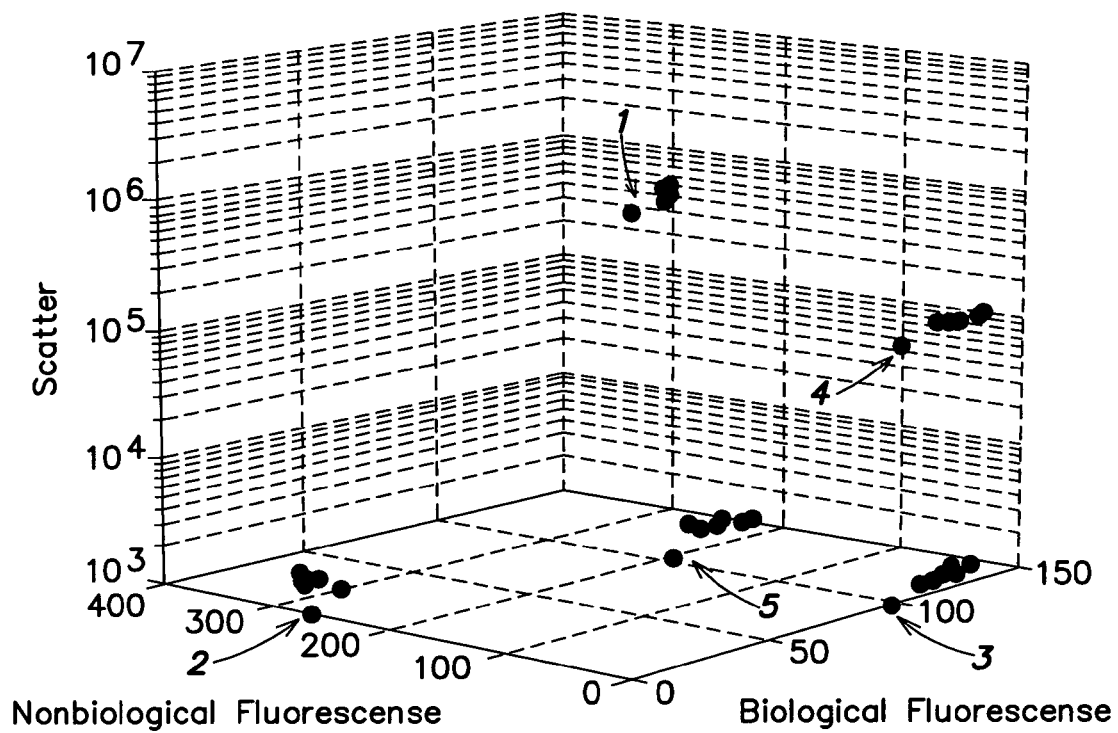
FIG. 8 is a map characterizing the nature of the various particles having responses shown in FIGS. 7A–7E and as discussed in the examples.

FIG. 8 is a map showing the relative positions of each of the constructed particles analyzed in Example 2 with respect to a scatter component, a non-biological fluorescence component, and a biological fluorescence component. The discriminant vectors for each of the dust grain 1, PAH mixture 2, spore 3, pollen 4, and spore with PAH 5 were mapped.

As shown, the spatial groupings provided an indicating of the general composition of particle. Thus, the technique of mapping can be utilized to facilitate the characterization of the nature of particles based on the particle's deconvolved response. Other representative discriminant vectors have also been shown for comparison.

As discussed above, other mapping techniques can be utilized to characterize the nature of each particle. For example, it may be possible to compute the ratios of short- and long-lifetime fluorescence to scatter, and plot ratios in two dimensions or to compute the ratio of short-lifetime fluorescence to long-lifetime fluorescence, and plot the ratio relative to scatter in two dimensions. It may also be possible to analyze groupings using statistical and geometrical algorithms, without using a graphical representation.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. For example, one or more detectors can be utilized in the systems and techniques of the present invention and, in accordance with some embodiments, a detector may be utilized or configured to measure a component of a composite emission decay profile; and in some cases, a second, typically separate detector can be utilized to measure a second component of the composite emission decay profile. Moreover, the time boundaries cited herein are approximate, typically based on the scientific literature, and may be adjusted and optimized for a variety or particular measurement situation. Further, the present invention has been described as characterizing an aerosol particle but need not be limited as such. Thus, one or more particles may be characterized, which can be airborne or otherwise. Accordingly, the foregoing description and drawings are by way of example only.

What is claimed is:

1. A system for classifying aerosol particles comprising:
    a detector capable of generating a signal corresponding to a composite emission decay profile of an emission from an aerosol particle; and
    means for deconvolving the signal into a discriminant vector that provides an indication of the nature of the aerosol particle.

2. A system for classifying aerosol particles comprising:
    a detector capable of generating a signal corresponding to a composite emission decay profile of an emission from a sample of aerosol particles; and
    a processor coupled to the detector to receive the signal, wherein the processor can determine a scatter component and a fluorescence component of the composite emission decay profile.

3. The system of claim 2, wherein the fluorescence component comprises a biological component and a non-biological component.

4. The system of claim 3, wherein the processor can determine a scatter intensity value corresponding to the scatter component.

5. The system of claim 4, wherein the processor can determine a non-biological fluorescence value corresponding to the non-biological component.

6. The system of claim 5, wherein the processor can determine a biological fluorescence value corresponding to the biological component.

7. The system of claim 2, further comprising a radiation source disposed to discharge electromagnetic energy to stimulate the emission from the sample.

8. A method of classifying an aerosol particle comprising:
    measuring a composite emission decay profile of an emission from the aerosol particle;
    determining a biological fluorescence time constant of the composite emission decay profile; and
    determining a biological emission constant of the composite emission decay profile.

9. The method of claim 8, further comprising stimulating the aerosol particle.

10. The method of claim 8, further comprising determining a scatter emission constant of the composite emission decay profile.

11. The method of claim 10, further comprising determining a non-biological fluorescence time constant of the composite emission decay profile.

12. The method of claim 11, further comprising determining a non-biological emission constant of the composite emission decay profile.

13. The method of claim 12, further comprising normalizing the scatter emission constant, the biological emission constant, and the non-biological emission constant relative to the scatter emission constant to produce a scatter component, a biological component, and a non-biological component.

14. The method of claim 13, further comprising mapping the scatter component relative to the biological component and the non-biological component to provide an indication of the nature of the aerosol particle.

15. The method of claim 12, further comprising determining a second biological fluorescence time constant of the composite emission decay profile.

16. The method of claim 15, further comprising determining a second biological emission constant of the composite emission decay profile.

17. The method of claim 12, further comprising determining a second non-biological time constant of the composite emission decay profile.

18. The method of claim 17, further comprising determining a second biological emission constant of the composite emission decay profile.

19. A method of classifying aerosol particles comprising:
stimulating the aerosol particles to promote radiation emission;
measuring a composite emission decay profile of the radiation emission, the composite emission decay profile comprising a scatter component, a first fluorescence component, and a second fluorescence component;
determining a scatter emission constant corresponding to the scatter component;
determining a first fluorescence emission constant of the composite emission decay profile; and
determining a second fluorescence emission constant of the composite emission decay profile.

20. The method of claim 19, further comprising deriving a first fluorescence time constant corresponding to the first fluorescence component.

21. The method of claim 20, further comprising deriving a second fluorescence time constant corresponding to the second fluorescence component.

22. The method of claim 19, further comprising determining a discriminant vector of the radiation emission as a function of the scatter emission constant, the first fluorescence emission constant, and the second fluorescence emission constant.

23. The method of claim 22, further comprising mapping the discriminant vector to provide an indication of the nature of the aerosol particle.

24. A method of classifying aerosol particles comprising:
measuring a composite emission from an aerosol particle;
deconvolving the composite emission to determine a discriminant vector of the aerosol particle; and
mapping the discriminant vector to provide an indication of the nature of the aerosol particle.

25. The method of claim 24, further comprising stimulating the aerosol particle to promote the composite emission.

26. The method of claim 24, wherein deconvolving the composite emission comprises determining a scatter emission constant and at least one of a biological emission constant and a non-biological emission constant.

* * * * *